United States Patent
Bluvshtein et al.

(10) Patent No.: US 11,894,695 B2
(45) Date of Patent: Feb. 6, 2024

(54) REPEATER RESONATOR

(71) Applicant: MINNETRONIX, INC., Saint Paul, MN (US)

(72) Inventors: Vlad Bluvshtein, Plymouth, MN (US); Lori Lucke, Rosemount, MN (US)

(73) Assignee: Minnetronix, Inc., St. Paul, MN (US)

( * ) Notice: Subject to any disclaimer, the term of this patent is extended or adjusted under 35 U.S.C. 154(b) by 504 days.

(21) Appl. No.: 16/258,960

(22) Filed: Jan. 28, 2019

(65) Prior Publication Data

US 2019/0157913 A1 May 23, 2019

Related U.S. Application Data

(62) Division of application No. 15/096,949, filed on Apr. 12, 2016, now Pat. No. 10,193,395.

(Continued)

(51) Int. Cl.
*H02J 50/50* (2016.01)
*A61M 60/148* (2021.01)
(Continued)

(52) U.S. Cl.
CPC ............ *H02J 50/50* (2016.02); *A61M 60/873* (2021.01); *H02J 50/12* (2016.02); *A61M 60/148* (2021.01); *A61M 2205/8243* (2013.01)

(58) Field of Classification Search
CPC ........ H02J 50/50; H02J 50/12; A61M 60/871; A61M 60/122; A61M 60/148; A61M 60/205; A61M 2205/8243

(Continued)

(56) References Cited

U.S. PATENT DOCUMENTS 3,195,540 A   7/1965   Waller
3,566,876 A   3/1971   Stoft et al.
(Continued)

FOREIGN PATENT DOCUMENTS

CN   203422610 U   2/2014
DE   102006037668 A1   3/2007
(Continued)

OTHER PUBLICATIONS

Mirbozorgi, et al., "A Transcutaneous Power Transfer Interface Based on a Multicoil Inductive Link", Aug. 28-Sep. 1, 2012, pp. 1659-1662, 34th Annual International Conference of the IEEE EMBS, San Diego, CA.

(Continued)

*Primary Examiner* — Rexford N Barnie
*Assistant Examiner* — Swarna N Chowdhuri
(74) *Attorney, Agent, or Firm* — Seager, Tufte & Wickhem, LLP

(57) ABSTRACT

A repeater for a wireless power transfer system is disclosed. The repeaters includes an elongated strip of material arranged in a substantially circular configuration with opposing ends of the elongated strip disposed in close proximity to each other, an inductive element associated with the elongated strip and arranged to provide a coupling with an adjacent resonator through flux directed outward from a first surface of the elongated strip, and a capacitive element associated with the elongated strip and arranged to resonate electromagnetic energy with the inductive element when the electromagnetic energy is transferred from the adjacent resonator through the coupling provided by the inductive element.

7 Claims, 13 Drawing Sheets

Related U.S. Application Data

(60) Provisional application No. 62/147,422, filed on Apr. 14, 2015.

(51) Int. Cl.
*H02J 50/12* (2016.01)
*A61M 60/873* (2021.01)

(58) Field of Classification Search
USPC .......................................................... 307/104
See application file for complete search history.

(56) References Cited

U.S. PATENT DOCUMENTS

| | | |
|---|---|---|
| 3,756,246 A | 9/1973 | Thaler et al. |
| 3,760,332 A | 9/1973 | Berkovits et al. |
| 3,806,807 A | 4/1974 | Nakamura |
| 3,943,535 A | 3/1976 | Schulman |
| 4,082,097 A | 4/1978 | Mann et al. |
| 4,143,661 A | 3/1979 | LaForge et al. |
| 4,164,946 A | 8/1979 | Langer |
| 4,221,543 A | 9/1980 | Cosentino et al. |
| 4,233,546 A | 11/1980 | Berthiaume |
| 4,237,895 A | 12/1980 | Johnson |
| 4,263,642 A | 4/1981 | Simmons et al. |
| 4,361,153 A | 11/1982 | Slocum et al. |
| 4,417,349 A | 11/1983 | Hills et al. |
| 4,439,806 A | 3/1984 | Brajder |
| 4,441,210 A | 4/1984 | Hochmair et al. |
| 4,446,513 A | 5/1984 | Clenet |
| 4,453,537 A | 6/1984 | Spitzer |
| 4,469,104 A | 9/1984 | Peers-Trevarton |
| 4,494,545 A | 1/1985 | Slocum et al. |
| 4,532,932 A | 8/1985 | Batty, Jr. |
| 4,561,443 A | 12/1985 | Hogrefe et al. |
| 4,625,730 A | 12/1986 | Fountain et al. |
| 4,665,896 A | 5/1987 | LaForge et al. |
| 4,681,111 A | 7/1987 | Silvian |
| 4,691,270 A | 9/1987 | Pruitt |
| 4,706,689 A | 11/1987 | Man |
| 4,768,512 A | 9/1988 | Imran |
| 4,774,950 A | 10/1988 | Cohen |
| 4,848,346 A | 7/1989 | Crawford |
| 4,855,888 A | 8/1989 | Henze et al. |
| 4,898,173 A | 2/1990 | Daglow et al. |
| 4,924,171 A | 5/1990 | Baba et al. |
| 4,925,443 A | 5/1990 | Heilman et al. |
| 4,933,798 A | 6/1990 | Widmayer et al. |
| 4,941,652 A | 6/1990 | Nagano et al. |
| 4,941,201 A | 7/1990 | Davis |
| 4,947,844 A | 8/1990 | McDermott |
| 4,953,068 A | 8/1990 | Henze |
| 4,964,027 A | 10/1990 | Cook et al. |
| 4,979,506 A | 12/1990 | Silvian |
| 5,012,807 A | 5/1991 | Stutz, Jr. |
| 5,076,270 A | 12/1991 | Stutz, Jr. |
| 5,132,888 A | 7/1992 | Lo et al. |
| 5,132,889 A | 7/1992 | Hitchcock et al. |
| 5,157,593 A | 10/1992 | Jain |
| 5,158,097 A | 10/1992 | Christlieb |
| 5,205,810 A | 4/1993 | Guiraudon et al. |
| 5,279,292 A | 1/1994 | Baumann et al. |
| 5,314,457 A | 5/1994 | Jeutter et al. |
| 5,327,335 A | 7/1994 | Maddali et al. |
| 5,345,375 A | 9/1994 | Mohan |
| 5,350,413 A | 9/1994 | Miller |
| 5,400,235 A | 3/1995 | Carroll |
| 5,413,595 A | 5/1995 | Stutz, Jr. |
| 5,438,498 A | 8/1995 | Ingemi |
| 5,444,608 A | 8/1995 | Jain |
| 5,456,715 A | 10/1995 | Liotta |
| 5,499,178 A | 3/1996 | Mohan |
| 5,500,004 A | 3/1996 | Ansourian et al. |
| 5,515,264 A | 5/1996 | Stacey |
| 5,522,865 A | 6/1996 | Schuman et al. |
| 5,559,689 A | 9/1996 | Kirchberg et al. |
| 5,569,156 A | 10/1996 | Mussivand |
| 5,569,307 A | 10/1996 | Schulman et al. |
| 5,584,870 A | 12/1996 | Single et al. |
| 5,594,635 A | 1/1997 | Gegner |
| 5,630,836 A | 5/1997 | Prem et al. |
| 5,662,692 A | 9/1997 | Paspa et al. |
| 5,674,281 A | 10/1997 | Snyder |
| 5,690,693 A | 11/1997 | Wang et al. |
| 5,702,427 A | 12/1997 | Ecker et al. |
| 5,702,431 A | 12/1997 | Wang et al. |
| 5,704,891 A | 1/1998 | Mussivand |
| 5,713,939 A | 2/1998 | Nedungadi et al. |
| 5,713,954 A | 2/1998 | Rosenberg et al. |
| 5,722,930 A | 3/1998 | Larson, Jr. et al. |
| 5,728,154 A | 3/1998 | Crossett et al. |
| 5,735,887 A | 4/1998 | Barreras, Sr. et al. |
| 5,741,314 A | 4/1998 | Daly et al. |
| 5,741,316 A | 4/1998 | Chen et al. |
| 5,749,909 A | 5/1998 | Schroeppel et al. |
| 5,751,125 A | 5/1998 | Weiss |
| 5,755,748 A | 5/1998 | Borza |
| 5,781,419 A | 7/1998 | Kutkut et al. |
| 5,945,762 A | 8/1999 | Chen et al. |
| 5,948,006 A | 9/1999 | Mann |
| 5,991,665 A | 11/1999 | Wang et al. |
| 5,995,874 A | 11/1999 | Borza |
| 6,047,214 A | 4/2000 | Mueller et al. |
| 6,058,330 A | 5/2000 | Borza |
| 6,067,474 A | 5/2000 | Schulman et al. |
| 6,076,016 A | 6/2000 | Feierbach |
| 6,088,619 A | 7/2000 | Hein et al. |
| 6,092,531 A | 7/2000 | Chen et al. |
| 6,112,121 A | 8/2000 | Paul et al. |
| 6,149,683 A | 11/2000 | Lancisi et al. |
| 6,212,430 B1 | 4/2001 | Kung |
| 6,233,485 B1 | 5/2001 | Armstrong et al. |
| 6,240,318 B1 | 5/2001 | Phillips |
| 6,254,525 B1 | 7/2001 | Reinhardt et al. |
| 6,263,247 B1 | 7/2001 | Mueller et al. |
| 6,275,737 B1 | 8/2001 | Mann |
| 6,324,430 B1 | 11/2001 | Zarinetchi et al. |
| 6,342,071 B1 | 1/2002 | Pless |
| 6,345,203 B1 | 2/2002 | Mueller et al. |
| 6,366,817 B1 | 4/2002 | Kung |
| 6,389,318 B1 | 5/2002 | Zarinetchi et al. |
| 6,400,991 B1 | 6/2002 | Kung |
| 6,424,867 B1 | 7/2002 | Snell |
| 6,430,444 B1 | 8/2002 | Borza |
| 6,434,194 B1 | 8/2002 | Eisenberg et al. |
| 6,442,434 B1 | 8/2002 | Zarinetchi et al. |
| 6,443,891 B1 | 9/2002 | Grevious |
| 6,451,055 B1 | 9/2002 | Weiss |
| 6,458,164 B1 | 10/2002 | Weiss |
| 6,478,820 B1 | 11/2002 | Weiss |
| 6,517,476 B1 | 2/2003 | Bedoya et al. |
| 6,579,315 B1 | 6/2003 | Weiss |
| 6,592,620 B1 | 7/2003 | Lancisi et al. |
| 6,641,612 B2 | 11/2003 | Pless |
| 6,648,914 B2 | 11/2003 | Berrang et al. |
| 6,671,554 B2 | 12/2003 | Gibson et al. |
| 6,810,289 B1 | 10/2004 | Shaquer |
| 6,831,944 B1 | 12/2004 | Misra et al. |
| 6,850,803 B1 | 2/2005 | Jimenez |
| 6,862,478 B1 | 3/2005 | Goldstein |
| 6,961,005 B2 | 11/2005 | Clement et al. |
| 6,978,181 B1 | 12/2005 | Snell |
| 7,003,353 B1 | 2/2006 | Parkhouse |
| 7,035,689 B1 | 4/2006 | Hawkins et al. |
| 7,062,331 B2 | 6/2006 | Zarinetchi et al. |
| 7,069,086 B2 | 6/2006 | Von Arx |
| 7,076,206 B2 | 7/2006 | Elferich et al. |
| 7,079,901 B1 | 7/2006 | Loftin et al. |
| 7,155,291 B2 | 12/2006 | Zarinetchi et al. |
| 7,173,411 B1 | 2/2007 | Pond |
| 7,191,007 B2 | 3/2007 | Desai et al. |
| 7,299,095 B1 | 11/2007 | Barlow et al. |
| 7,317,947 B2 | 1/2008 | Wahlstrand et al. |
| 7,471,986 B2 | 12/2008 | Hatlestad |

(56) References Cited

U.S. PATENT DOCUMENTS

| | | |
|---|---|---|
| 7,512,443 B2 | 3/2009 | Phillips et al. |
| 7,515,967 B2 | 4/2009 | Phillips |
| 7,574,262 B2 | 8/2009 | Haugland et al. |
| 7,599,743 B2 | 10/2009 | Hassler, Jr. et al. |
| 7,672,732 B2 | 3/2010 | Sun et al. |
| 7,738,965 B2 | 6/2010 | Phillips et al. |
| 7,774,069 B2 | 8/2010 | Olson |
| 7,781,916 B2 | 8/2010 | Boys |
| 7,822,480 B2 | 10/2010 | Park et al. |
| 7,848,814 B2 | 12/2010 | Torgerson et al. |
| 7,962,211 B2 | 6/2011 | Torgerson et al. |
| 8,024,047 B2 | 9/2011 | Olson et al. |
| 8,027,735 B1 | 9/2011 | Tziviskos et al. |
| 8,032,486 B2 | 10/2011 | Townsend et al. |
| 8,050,068 B2 | 11/2011 | Hussmann et al. |
| 8,093,758 B2 | 1/2012 | Hussmann |
| 8,097,983 B2 | 1/2012 | Karalis et al. |
| 8,116,681 B2 | 2/2012 | Baarman |
| 8,126,563 B2 | 2/2012 | Ibrahim |
| 8,265,770 B2 | 9/2012 | Toy et al. |
| 8,311,638 B2 | 11/2012 | Aghassian |
| 8,428,712 B2 | 4/2013 | Davis et al. |
| 8,428,724 B2 | 4/2013 | Sage |
| 8,437,855 B2 | 5/2013 | Sjostedt et al. |
| 8,457,758 B2 | 6/2013 | Olson |
| 8,473,066 B2 | 6/2013 | Aghassian et al. |
| 8,515,112 B2 | 8/2013 | Crawford et al. |
| 8,543,209 B2 | 9/2013 | Tyers et al. |
| 8,626,308 B2 | 1/2014 | Meskens |
| 8,630,717 B2 | 1/2014 | Olson et al. |
| 8,676,337 B2 | 3/2014 | Kallmyer |
| 8,706,255 B2 | 4/2014 | Philips et al. |
| 8,738,148 B2 | 5/2014 | Olson et al. |
| 8,764,621 B2 | 6/2014 | Badstibner et al. |
| 8,766,788 B2 | 7/2014 | D'Ambrosio |
| 8,903,515 B2 | 12/2014 | Mashiach |
| 8,912,687 B2 | 12/2014 | Kesler et al. |
| 8,972,012 B2 | 3/2015 | Lim |
| 9,192,772 B1 | 11/2015 | Kishiyama et al. |
| 9,603,984 B2 | 3/2017 | Romero et al. |
| 9,855,376 B2 | 1/2018 | Bluvshtein et al. |
| 10,149,933 B2 | 12/2018 | Bluvshtein et al. |
| 10,193,395 B2 | 1/2019 | Bluvshtein et al. |
| 10,342,908 B2 | 7/2019 | Bluvshtein et al. |
| 10,376,625 B2 | 8/2019 | Bluvshtein et al. |
| 10,406,267 B2 | 9/2019 | Lucke et al. |
| 2002/0021226 A1 | 2/2002 | Clement et al. |
| 2002/0032471 A1 | 3/2002 | Loftin et al. |
| 2002/0087204 A1 | 7/2002 | Kung et al. |
| 2002/0128709 A1 | 9/2002 | Pless |
| 2002/0177884 A1 | 11/2002 | Ahn et al. |
| 2003/0045912 A1 | 3/2003 | Williams et al. |
| 2003/0085684 A1 | 5/2003 | Tsukamoto et al. |
| 2003/0171792 A1 | 9/2003 | Zarinetchi et al. |
| 2004/0034393 A1 | 2/2004 | Hansen et al. |
| 2004/0039423 A1 | 2/2004 | Dolgin |
| 2004/0049245 A1 | 3/2004 | Gass et al. |
| 2005/0065570 A1 | 3/2005 | Stein et al. |
| 2005/0075694 A1 | 4/2005 | Schmeling et al. |
| 2005/0075696 A1 | 4/2005 | Forsberg et al. |
| 2005/0131491 A1 | 6/2005 | Shaquer |
| 2005/0245996 A1 | 11/2005 | Phillips et al. |
| 2005/0288739 A1 | 12/2005 | Hassler et al. |
| 2005/0288741 A1 | 12/2005 | Hassler et al. |
| 2006/0020305 A1 | 1/2006 | Desai et al. |
| 2006/0036127 A1 | 2/2006 | Delgado, III |
| 2006/0167333 A1 | 7/2006 | Moore et al. |
| 2006/0184204 A1 | 8/2006 | He |
| 2006/0247737 A1 | 11/2006 | Olson |
| 2006/0267790 A1 | 11/2006 | Matthiessen et al. |
| 2007/0060787 A1 | 3/2007 | Peters et al. |
| 2007/0255349 A1 | 11/2007 | Torgerson et al. |
| 2007/0255350 A1 | 11/2007 | Torgerson et al. |
| 2008/0065173 A1 | 3/2008 | Wahlstrand et al. |
| 2008/0198947 A1 | 8/2008 | Zierhofer |
| 2008/0255631 A1 | 10/2008 | Sjostedt et al. |
| 2008/0303480 A1 | 12/2008 | Prutchi et al. |
| 2009/0067653 A1 | 3/2009 | Meskens et al. |
| 2009/0281597 A1 | 11/2009 | Parramon et al. |
| 2010/0010582 A1 | 1/2010 | Carbunaru et al. |
| 2010/0033023 A1 | 2/2010 | Baarman |
| 2010/0033240 A1 | 2/2010 | Denison et al. |
| 2010/0063347 A1 | 3/2010 | Yomtov et al. |
| 2010/0164296 A1 | 7/2010 | Kurs et al. |
| 2010/0249886 A1 | 9/2010 | Park et al. |
| 2010/0268305 A1 | 10/2010 | Olson |
| 2010/0292759 A1 | 11/2010 | Hahn |
| 2010/0327887 A1 | 12/2010 | Denison et al. |
| 2011/0004278 A1 | 1/2011 | Aghassian et al. |
| 2011/0093048 A1 | 4/2011 | Aghassian |
| 2011/0101790 A1 | 5/2011 | Budgett |
| 2011/0106210 A1 | 5/2011 | Meskens |
| 2011/0248574 A1* | 10/2011 | Yamamoto ............ H02J 50/70 307/104 |
| 2011/0301669 A1 | 12/2011 | Olson |
| 2011/0313490 A1 | 12/2011 | Parramon et al. |
| 2012/0032522 A1* | 2/2012 | Schatz ................ A61N 1/3975 307/104 |
| 2012/0095528 A1 | 4/2012 | Miller, III et al. |
| 2012/0154143 A1 | 6/2012 | D'Ambrosio |
| 2012/0157753 A1 | 6/2012 | D'Ambrosio |
| 2012/0157754 A1 | 6/2012 | D'Ambrosio |
| 2012/0197352 A1 | 8/2012 | Carbunaru et al. |
| 2012/0215285 A1 | 8/2012 | Tahmasian |
| 2012/0265003 A1 | 10/2012 | D'Ambrosio et al. |
| 2013/0023958 A1 | 1/2013 | Fell |
| 2013/0041429 A1 | 2/2013 | Aghassian |
| 2013/0043736 A1 | 2/2013 | Zilbershlag |
| 2013/0046361 A1 | 2/2013 | DiGiore et al. |
| 2013/0123881 A1 | 5/2013 | Aghassian |
| 2013/0127253 A1 | 5/2013 | Stark |
| 2013/0158631 A1 | 6/2013 | Shea et al. |
| 2013/0163688 A1 | 6/2013 | Calvin |
| 2013/0278226 A1 | 10/2013 | Cong et al. |
| 2013/0310629 A1* | 11/2013 | Lafontaine ............ H02J 50/50 600/16 |
| 2013/0317345 A1 | 11/2013 | Frustaci et al. |
| 2013/0331638 A1 | 12/2013 | Cameron et al. |
| 2013/0338734 A1 | 12/2013 | Hoyer et al. |
| 2014/0005749 A1 | 1/2014 | Stahmann et al. |
| 2014/0015338 A1* | 1/2014 | Yoshino ................ H02J 50/12 307/104 |
| 2014/0021798 A1* | 1/2014 | Kesler ................ H02J 7/00045 307/104 |
| 2014/0031607 A1 | 1/2014 | Zilbershlag et al. |
| 2014/0139034 A1 | 5/2014 | Sankar et al. |
| 2014/0243944 A1 | 8/2014 | Stevenson et al. |
| 2014/0371823 A1 | 12/2014 | Mashiach et al. |
| 2015/0069847 A1 | 3/2015 | Meyer et al. |
| 2015/0073203 A1 | 3/2015 | Wariar et al. |
| 2015/0207331 A1 | 7/2015 | Petersen |
| 2015/0209591 A1 | 7/2015 | Meskens |
| 2015/0333801 A1 | 11/2015 | Hosotani |
| 2015/0364861 A1 | 12/2015 | Lucke et al. |
| 2015/0380988 A1 | 12/2015 | Chappell et al. |
| 2016/0175600 A1 | 6/2016 | Amir et al. |
| 2016/0197511 A1 | 7/2016 | Atasoy et al. |
| 2016/0206799 A1 | 7/2016 | Lucke et al. |
| 2016/0248265 A1* | 8/2016 | Oo ........................ H02J 7/0042 |
| 2016/0294225 A1 | 10/2016 | Blum et al. |
| 2016/0303301 A1 | 10/2016 | Bluvshtein et al. |
| 2017/0119947 A1 | 5/2017 | Eldridge et al. |
| 2018/0207338 A1 | 7/2018 | Bluvshtein et al. |
| 2019/0111198 A1 | 4/2019 | Bluvshtein et al. |

FOREIGN PATENT DOCUMENTS

| | | |
|---|---|---|
| DE | 102015112097 A1 | 1/2016 |
| FR | 2587221 | 3/1987 |
| JP | 2597623 B2 | 4/1997 |
| WO | 8301006 | 3/1983 |
| WO | 8700420 | 1/1987 |
| WO | 9809588 | 3/1998 |

(56) References Cited

FOREIGN PATENT DOCUMENTS

| WO | 0191678 | A1 | 12/2001 |
| WO | 2007126454 | A2 | 11/2007 |
| WO | 2008106717 | A1 | 9/2008 |
| WO | 2009029977 | A1 | 3/2009 |
| WO | 2010042057 | A1 | 4/2010 |
| WO | 2010133702 | A2 | 11/2010 |
| WO | 2011119352 | A1 | 9/2011 |
| WO | 2012077088 | A2 | 6/2012 |
| WO | 2012077088 | A3 | 6/2012 |
| WO | 2014036449 | A1 | 3/2014 |
| WO | 2014169940 | A1 | 10/2014 |

OTHER PUBLICATIONS

Ng, et al., "Wireless Power Delivery for Retinal Prostheses", 33rd Annual International Conference of the IEEE EMBS, pp. 8356-8360, Aug. 30-Sep. 3, 2011, Boston MA.

First Office Action for German Patent Application No. 102016106683.4, dated Mar. 4, 2018, with English Translation (17 pages).

"Modulator (in German)", Wikipedia Version Mar. 28, 2013.

Andia, et al., "Closed Loop Wireless Power Transmission for Implantable Medical Devices," IEEE, 2011, pp. 404-407.

Bonsor, , "How Artificial Hearts Work," HowStuffWorks, Aug. 9, 2001, downloaded from HowStuffWorks.com. at http://science.howstuffworks.com/innovation/everyday-innovations/artificial-heart.htm (12 pages).

Knecht, et al., "Optimization of Transcutaneous Energy Transfer Coils for High Power Medical Applications," Workshop on Control and Modeling for Power Electronics (COMPEL), 2014, pp. 1-10.

Ng, et al., "Closed-Loop Inductive Link for Wireless Powering of a High Density Electrode Array Retinal Prosthesis," IEEE, 2009, pp. 92-97.

Ng, et al., "Wireless Power Delivery for Retinal Prostheses," 33rd Annual International Conference of the IEEE EMBS, Aug. 30, 2011-Sep. 3, 2011, pp. 8356-8360.

Shmilovitz, et al., "Noninvasive Control of the Power Transferred to an Implanted Device by an Ultrasonic Transcutaneous Energy Transfer Link," IEEE Transactions on Biomedical Engineering, Apr. 2014, pp. 995-1004, vol. 61, No. 4.

\* cited by examiner

REPEATER RESONATOR

CROSS-REFERENCE TO RELATED APPLICATIONS

This application is a divisional of U.S. patent application Ser. No. 15/096,949, filed Apr. 12, 2016 and entitled "REPEATER RESONATOR," which claims the benefit of U.S. Provisional Patent Application No. 62/147,422, filed Apr. 14, 2015 and entitled "REPEATOR RESONATOR." The entirety of each of which is herein incorporated by reference.

TECHNICAL FIELD

The technology described herein relates to a repeater for a wireless power transfer system and to a wireless power transfer system that includes one or more repeaters.

BACKGROUND

Wireless power transfer systems are increasingly used in many applications. For example, there is a need to deliver electric power to implanted medical devices such as artificial hearts and ventricle assist devices. Through the use of wireless power transfer systems it is possible to deliver power non-invasively through electromagnetic energy transmitted through the skin. This technology can provide life sustaining benefits. However, those who use the technology may suffer reduced mobility or other inconveniences. For example, a subject within whom a medical device is implanted may be somewhat tethered to the electrical power cords and devices that provide the continuous power needed for some devices, such as ventricle assist devices. Thus, the ability of the subject to move about or to take part in certain activities such as swimming may be limited or non-existent. Additionally, wireless power transfer systems can be sensitive to changes in orientations of certain components. These orientation changes can result in lost coupling between adjacent components. As a result, power transfer can be become inefficient or non-existent. Prior art systems fail to provide mechanisms for addressing these and other issues. These and other deficiencies of the prior art are addressed herein.

SUMMARY

In one aspect, the present disclosure is directed to a repeater for a wireless power transfer system, including an elongated strip of material arranged in a substantially circular configuration with opposing ends of the elongated strip disposed in close proximity to each other, an inductive element associated with the elongated strip and arranged to provide a coupling with an adjacent resonator through flux directed outward from a first surface of the elongated strip, and a capacitive element associated with the elongated strip and arranged to resonate electromagnetic energy with the inductive element when the electromagnetic energy is transferred from the adjacent resonator through the coupling provided by the inductive element.

In some implementations, the inductive element includes a conductive pathway arranged along a perimeter of the elongated strip of material.

In some implementations, the inductive element includes a plurality of coils arranged along a length of the elongated strip of material.

In some implementations, the coupling between the repeater and the adjacent resonator is independent of an angular position of the repeater.

In some implementations, the coupling between the repeater and the adjacent resonator is independent of a position of the resonator along a length of the repeater.

In some implementations, the adjacent resonator is a first resonator and at least a portion of the electromagnetic energy that resonates between the inductive and capacitive elements transfers to a second resonator through the coupling provided by the flux directed outward from the first surface.

In some implementations, the first resonator is electrically connected to a power source, and the second resonator is connected to a circuit load.

In some implementations, the circuit load is an implanted medical device, the second resonator is an implanted power transfer coil arranged to provide power to the implanted medical device, and the repeater is configured to transfer power to the second resonator through the skin of a subject within whom the medical device and the second resonator are implanted.

In some implementations, the repeater is configured to be worn around the waist of the subject within whom the medical device and the second resonator are implanted.

In some implementations, the repeater is embedded within a garment worn by the subject within whom the medical device and the second resonator are implanted.

In another aspect, the present disclosure is directed to a wireless power transfer system, including a first resonator, a repeater resonator inductively coupled to the first resonator and configured to receive electromagnetic energy from the first resonator, the coupling between the repeater and the first resonator being independent of an angular position of the repeater, and a second resonator inductively coupled to the repeater and configured to receive electromagnetic energy from the repeater, the coupling between the second resonator and the repeater being independent of the angular position of the repeater.

In some implementations, the coupling between the repeater and the first and second resonators is independent of a position of the first and second resonators along a length of the repeater.

In some implementations, the first resonator is electrically connected to a power source and configured as a transmitter; and the second resonator is electrically connected to a circuit load and configured as a receiver.

In some implementations, the circuit load is an implanted medical device, the second resonator is an implanted power transfer coil arranged to provide power to the implanted medical device, and the repeater is configured to be worn around the waist of a subject within whom the medical device and the second resonator are implanted, the repeater further configured to transfer power to the second resonator through the skin of the subject.

In some implementations, the first resonator includes an array of power transmission coils embedded within a mattress.

In some implementations, the first resonator includes an array of power transmission coils embedded with a chair.

In some implementations, the repeater resonator is a first resonator and at least one of the first and second resonators is a second repeater resonator.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

Figure 1:
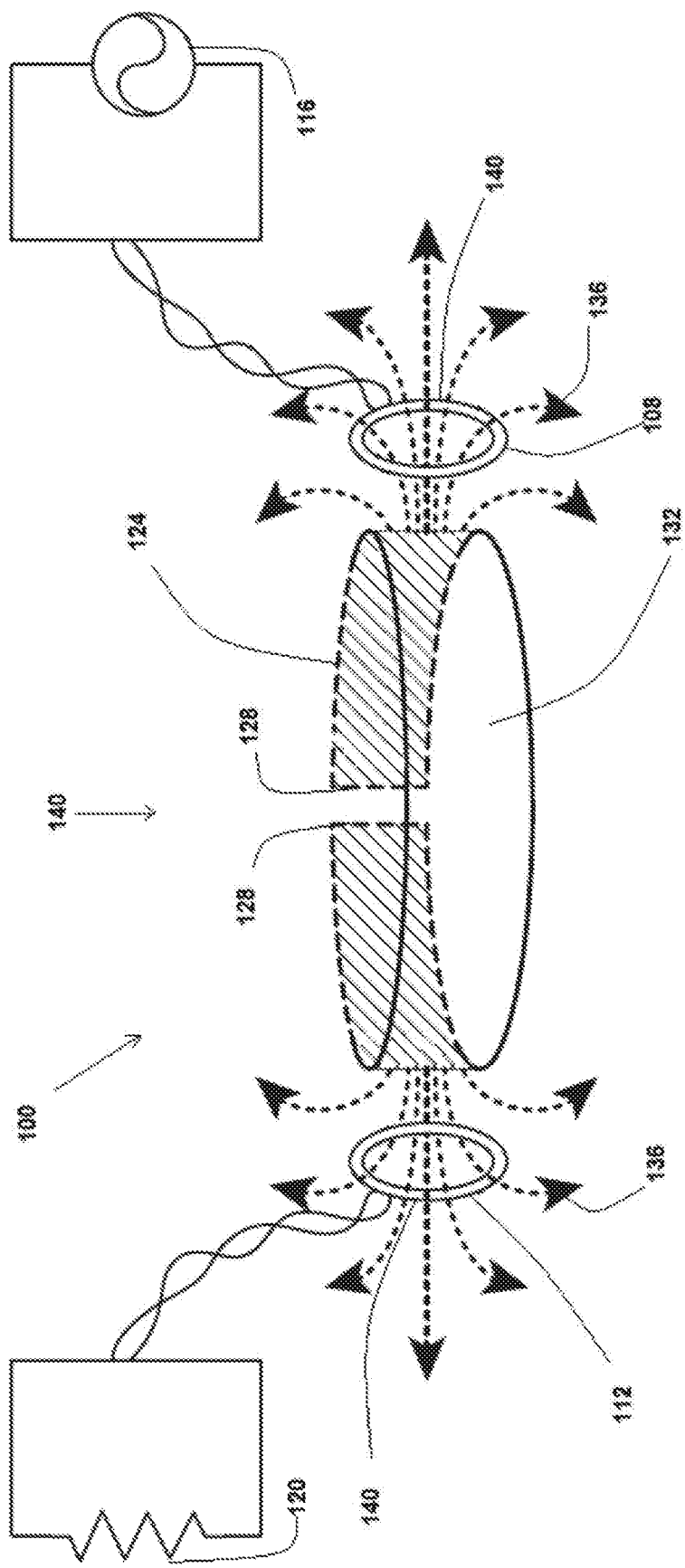
FIG. 1 is a schematic illustration of a wireless power transfer system that includes an orientable repeater in accordance with the present disclosure.

The present disclosure is directed to an orientable repeater for a wireless power transfer system. An orientable repeater in accordance with the present disclosure may be interposed between the transmitter and the receiver of a wireless power transfer system so as to extend the overall distance across which the wireless power transfer system operates. The repeater is "orientable" in the sense that it may be disposed in various orientations with respect to adjacent components such as the receiver, the transmitter or, in some cases, an additional repeater. The orientable repeater is configured to maintain coupling between itself and an adjacent component across various angular positions for either the repeater or the adjacent component. In this way, the orientable repeater tolerates what would otherwise be a misalignment that could result in lost coupling.

Generally, a wireless power transfer system is configured to transfer electric power across a distance through the use of coupled electromagnetic resonators. An electromagnetic resonator operates by shifting electromagnetic energy at a certain frequency between energy storage components, such as capacitive and inductive elements. An electromagnetic resonator generally has a resonance frequency at which the energy transfer between capacitive and inductive elements is optimal. Energy transfer may occur between adjacent electromagnetic resonators when the resonators are positioned such that the magnetic near fields of the resonators interact. The interaction between the magnetic near fields couples the adjacent resonators such that a portion of the electromagnetic energy that shifts between energy storage components in one resonator transfers to the adjacent resonator. The proportion of the total energy that transfers to the adjacent resonator is dependent on the amount of coupling that exists between the adjacent resonators. The amount of coupling between adjacent resonators is generally dependent on the relative geometries of the resonators and the distance by which the resonators are separated.

In a wireless power transfer system, a first electromagnetic resonator is configured as the transmitter and is thus electrically connected to a power supply or power source. A second electromagnetic resonator is configured as the receiver and is thus electrically connected to a circuit load. The receiver and the transmitter may be tuned or otherwise configured for resonance at the same or similar frequencies. When the power source drives the transmitter with an alternating current, electrical power is transferred, via the coupling between the transmitter and the receiver, to the receiver and thus to the circuit load. The coupling that exists in a wireless power transfer system is generally a function of the separation distance between the transmitter and the receiver. In a magnetic resonant system that relies on inductive coupling with a low quality factor (Q-factor), the transmitter and the receiver must be fairly close to each other in order for energy transfer to take place. In a highly resonant magnetic system with a high Q-factor, energy transfer may take place with the transmitter and the receiver separated by a greater distance. In either case, once the transmitter and receiver are separated past a certain distance, coupling is lost and power transfer is no longer possible.

A repeater may be used to achieve power transfer across distances that are greater that what is possible with only a receiver and transmitter in a highly resonant magnetic system. A repeater is an electromagnetic resonator that may be interposed between the receiver and transmitter to extend the distance across which a wireless power transfer system operates. Like the transmitter and receiver components, the repeater operates by shifting electromagnetic energy at a certain frequency between energy storage components, such as capacitive and inductive elements. The repeater may be configured to resonate at the same resonance frequency as that of the transmitter and the receiver. When positioned in place, the repeater couples to both the receiver and the transmitter. When the power source drives the transmitter with an alternating current, electrical power is transferred from the transmitter to the repeater, which in turn transfers the power to the receiver. The amount of energy transferred to or from the repeater is dependent on the amount of coupling that exists between the repeater and the transmitter or receiver. As mentioned, the amount of coupling is generally dependent on the relative geometries of the resonators and the distance by which the resonators are separated. Additionally, the orientation of the repeater may affect the amount of coupling. Conventional repeaters that are constructed as planar coils must be arranged in a substantially parallel orientation with respect to the transmitter and receiver in order for the amount of coupling to be sufficient for an effective power transfer. Conventional repeaters are limited to this substantially parallel orientation because their planar construction results in a magnetic near field that extends perpendicularly outward from the plane of the coil. When the coil is rotated away from the substantially parallel orientation, the magnetic field rotates away from the receiver or transmitter and coupling is lost.

FIG. 1 is a schematic illustration of a wireless power transfer system 100 that includes an orientable repeater 104 in accordance with the present disclosure. The orientable repeater 104 may be interposed between a transmitter 108 and a receiver 112 of the wireless power transfer system 100. The transmitter 108 and the receiver 112 may be generally configured as electromagnetic resonators. The transmitter 108 may be electrically connected to a power source 116. The receiver 112 may be connected to a circuit load 120. In operation, the power source 116 drives the transmitter 108 with an alternating current. Electrical power is transferred to the repeater 104 via coupling that exists between the transmitter 108 and the repeater 104. From the repeater 104, electrical power is transferred to the receiver 112 via coupling that exists between the repeater 104 and the receiver 112. From the receiver 112, electrical power is then transferred to the circuit load 120. With the orientable repeater 104 in place, power transfer may be achieved across distances that are greater that what would be possible with only the transmitter 108 and the receiver 112.

Figure 2A:
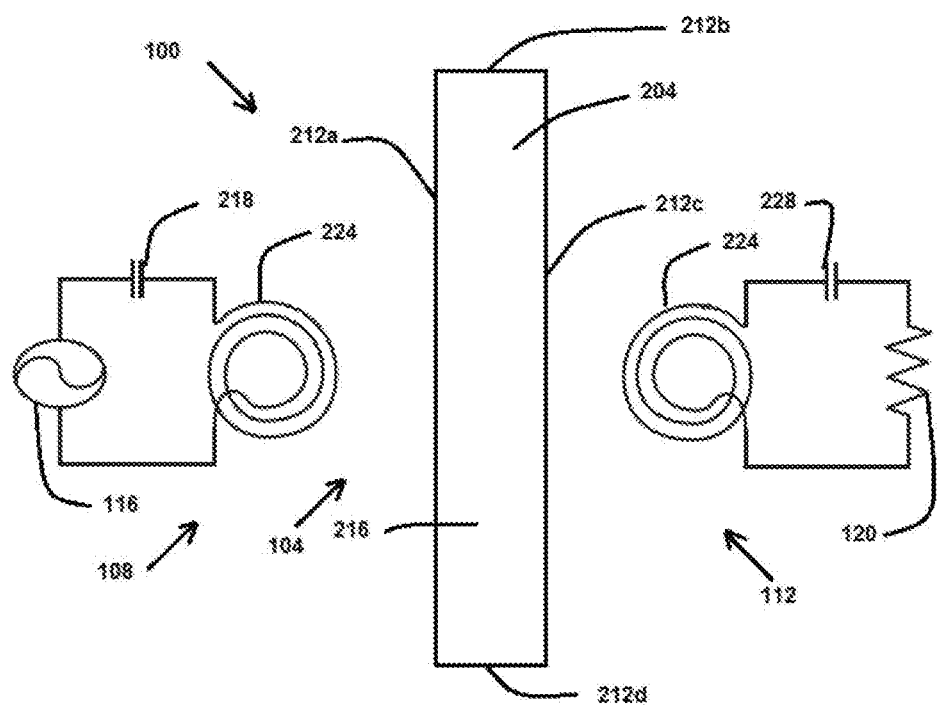
FIG. 2A is a circuit diagram for the wireless power transfer system that includes an orientable repeater embodiment arranged as an inductive track.
Figure 2B:
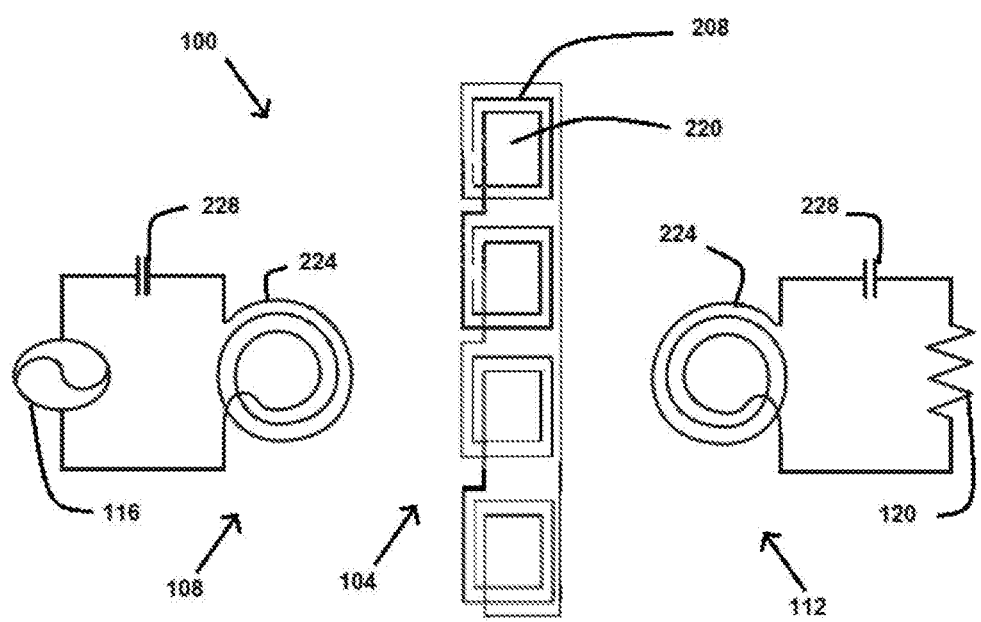
FIG. 2B is a circuit diagram for the wireless power transfer system that includes an orientable repeater embodiment arranged as a series of coils.

As shown in FIG. 1, an orientable repeater 104 may be configured as an elongated strip of material 124 having opposing ends 128. The opposing ends 128 are brought together or otherwise arranged to be in close proximity to each other. The remainder of the elongated strip of material 124 extends between the opposing ends 128 in a substantially circular configuration. The orientable repeater 104 is generally configured as an electromagnetic resonator that inductively couples to a transmitter 108 and to a receiver 112, each of which may be adjacent to an outwardly facing surface 132 of the strip of material 124. The orientable repeater 104 may be configured to shift electromagnetic energy at certain frequencies between energy storage components, such as capacitive and inductive elements. The orientable repeater 104 may be configured for resonance at substantially the frequency as that of the transmitter 108 and the receiver 112 so as to effectively transfer energy via the inductive coupling. Various embodiments of the orientable repeater 104 are illustrated in FIGS. 2A-B, each of which achieves this functionality. FIG. 2A is a circuit diagram for the wireless power transfer system 100 that shows an orientable repeater 104 arranged as an inductive track 204. FIG. 2B is a circuit diagram for the wireless power transfer system 100 that shows an orientable repeater 104 arranged as a series of coils 208. FIGS. 2A-B also show circuit diagram representations for the transmitter 108 and the receiver 112.

Figure 3A:
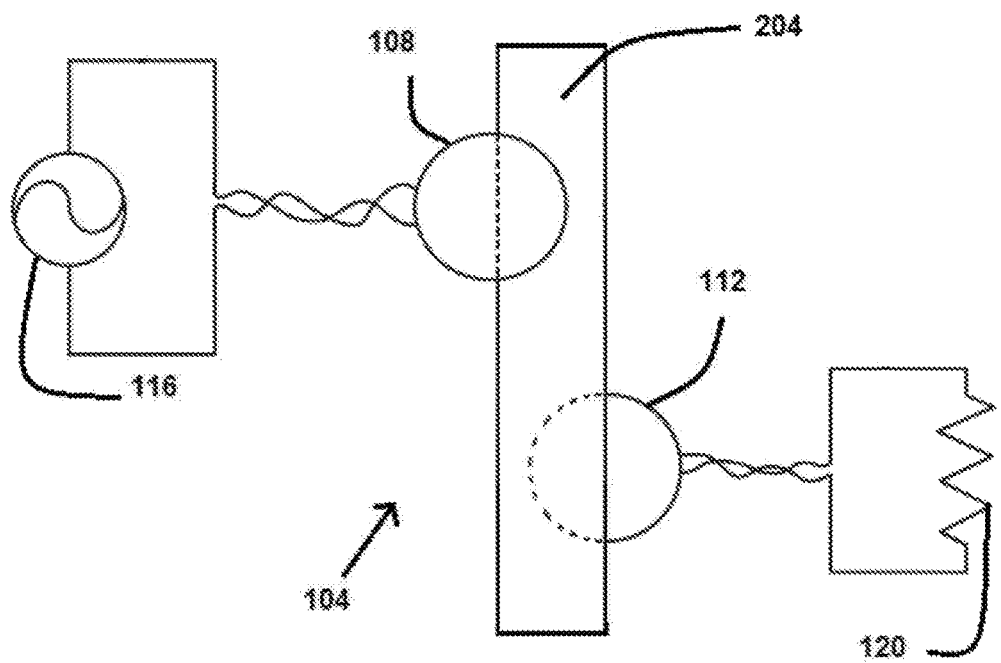
FIG. 3A is a schematic illustration of the wireless power transfer system of FIG. 2A.

Turing first to the orientable repeater 104 arranged as an inductive track 204, reference is made to FIG. 2A. In this embodiment, the orientable repeater 104 includes wires or other conductors 212a-d that are arranged along the perimeter or edges of the inductive track 204. Current that is induced in the orientable repeater 104 from an adjacent resonator such as the transmitter 108 travels along the perimeter of the inductive track 204 through the conductors 212a-d. The interior region 216 of the orientable repeater 104 that is adjacent to the conductors 212a-d is non-conductive. In this arrangement, the conductors 212a-d form a loop around the non-conductive interior region 216 and in so doing from an inductor. This inductor serves as an energy storage component for the orientable repeater 104. The orientable repeater 104 may include parasitic capacitors or other capacitive elements that form a second energy storage element. The orientable repeater 104 resonates by shifting energy between these two energy storage elements. The energy may be transferred to the orientable repeater 104 via a coupling that corresponds to near field magnetic flux that pass through the loop formed by the conductors 212a-d. Energy may be transferred away from the orientable repeater 104 via this same near field magnetic flux. Because the magnetic flux passes through the loop formed by the conductors 212a-d, an orientable repeater 104 arranged as an inductive track 204 may couple to a resonator that is adjacent to the outwardly facing surface 132 of the orientable repeater 104. This aspect of the orientable repeater 104 arranged as an inductive track 204 is further illustrated in FIG. 3A.

Figure 3B:
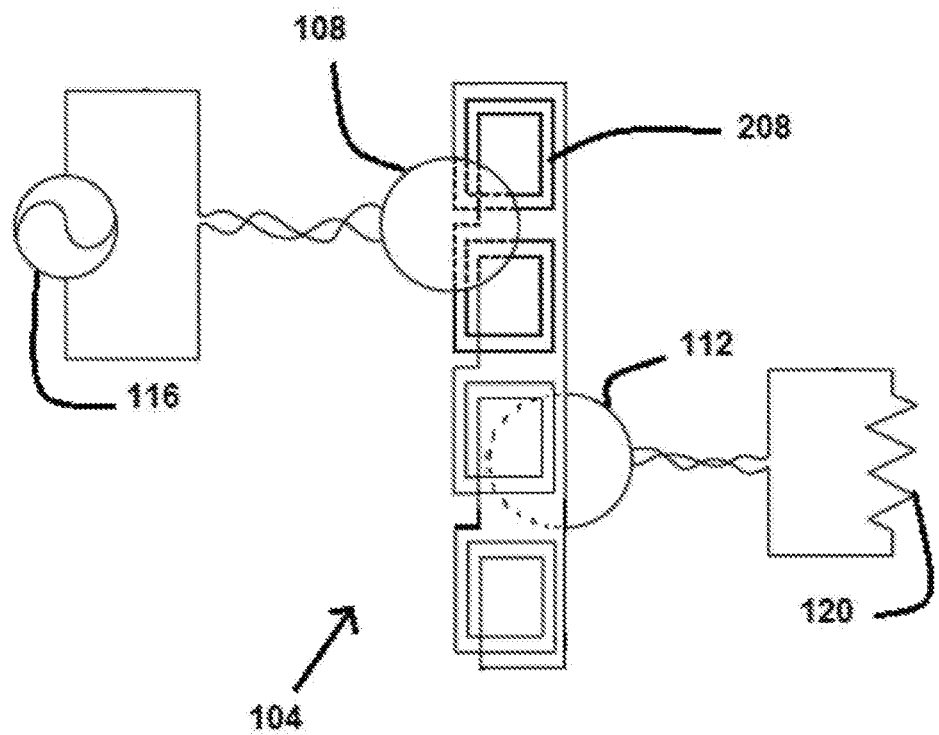
FIG. 3B is a schematic illustration of the wireless power transfer system of FIG. 2B.

Turing now to the orientable repeater 104 arranged as a series of coils 208, reference is made to FIG. 2B. In this embodiment, the orientable repeater 104 includes a plurality of coils 208 arranged along the length of the repeater 104. Current that is induced in the orientable repeater 104 from an adjacent resonator such as the transmitter 108 travels through these coils 208 and down the length of the repeater 104. The interior regions 220 of the coils 208 are non-conductive. In this arrangement, the coils 208 form loops around the non-conductive interior regions 220 and in so doing from inductors. These inductors serve as an energy storage component for the orientable repeater 104. The orientable repeater 104 may include parasitic capacitors or other capacitive elements that form a second energy storage element. The orientable repeater 104 resonates by shifting energy between these two energy storage elements. The energy may be transferred to the orientable repeater 104 via a coupling that corresponds to near field magnetic flux that passes through the loops formed by coils 208. Energy may be transferred away from the orientable repeater 104 via this same near field magnetic flux. Because the magnetic flux passes through the loops formed by the coils 208, an orientable repeater 104 arranged as a series of coils 208 may couple to a resonator that is adjacent to the outwardly facing surface 132 of the orientable repeater 104. This aspect of the orientable repeater 104 arranged as a series of coils 208 is further illustrated in FIG. 3B.

The magnetic flux that provides for coupling to a resonator that is adjacent to the outwardly facing surface 132 of the orientable repeater 104 is generally indicated in FIG. 1 with reference numeral 136. The magnetic flux 136 extends outwardly as illustrated in FIG. 1 whether the orientable repeater 104 is configured as an inductive track 204 or as a series of coils 208. Thus, in one respect, FIG. 1 illustrates the coupling that is established between the orientable repeater 104 and the transmitter 108. In another respect, FIG. 1 illustrates the coupling that is established between the orientable repeater 104 and the receiver 112. As shown in FIGS. 1 and 2A-B, the transmitter 108 and the receiver 112 may be configured as conventional planar coils 140 that include inductive 224 and capacitive 228 energy storage elements. In this configuration, energy may be transferred to and from the transmitter 108 and the receiver 112 through magnetic flux lines that pass through the loop formed by the coils 140. Thus, the transmitter 108 and the receiver 112 will couple to the orientable repeater 104 provided that the transmitter 108 and the receiver 112 are not oriented perpendicularly with respect to the outwardly facing surface 132 of the orientable repeater 104. More specifically, a transmitter 108 or receiver 112 that is positioned adjacent to a given point along the length of the orientable repeater 104 and oriented to be at least not perpendicular with respect to the outwardly facing surface 132 may couple to the orientable repeater 104. Whether the orientable repeater 104 is configured as an inductive track 204 or as series of coils 208, the orientable repeater 104 provides a plurality of power transfer points along the length of the orientable repeater 104. More specifically, power transfer may be affected by placing the orientable repeater 104 in contact or in proximity to the transmitter 108 or the receiver 112 at any point along the orientable repeater 104.

Figure 4:
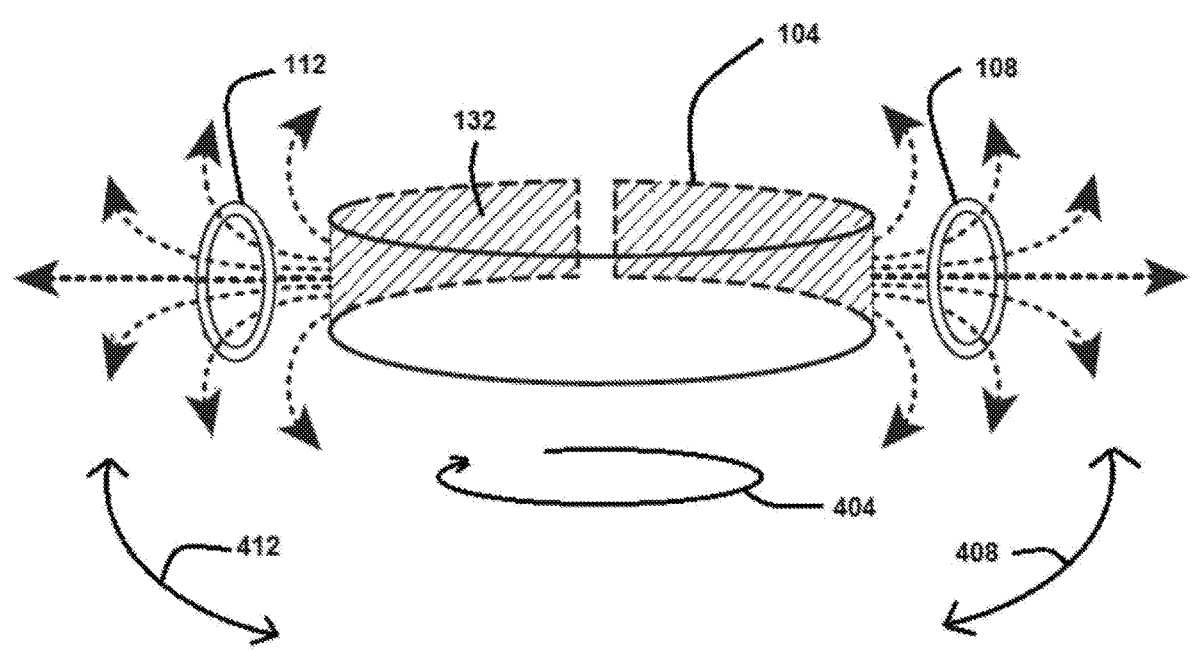
FIG. 4 is a schematic illustration of the wireless power transfer system of FIG. 1 that illustrates how the coupling between the orientable repeater and an adjacent resonator is independent of an angular orientation of the repeater and a position of the resonator.
Figure 5A:
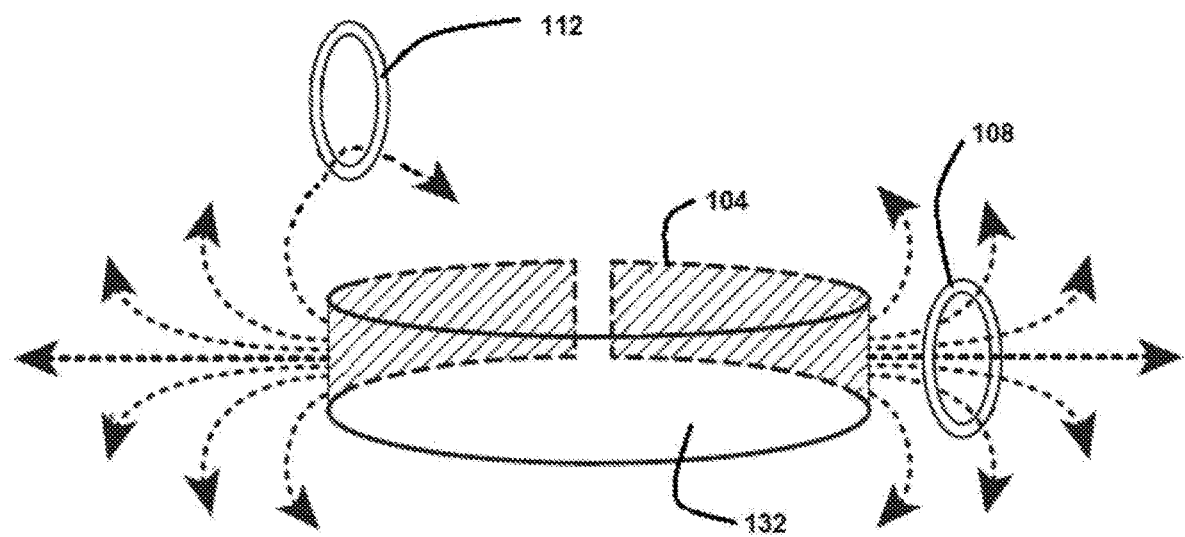
FIGS. 5A and B are a schematic illustrations of the wireless power transfer system of FIG. 1 that illustrates further coupling positions for the resonator adjacent to an orientable repeater.
Figure 5B:
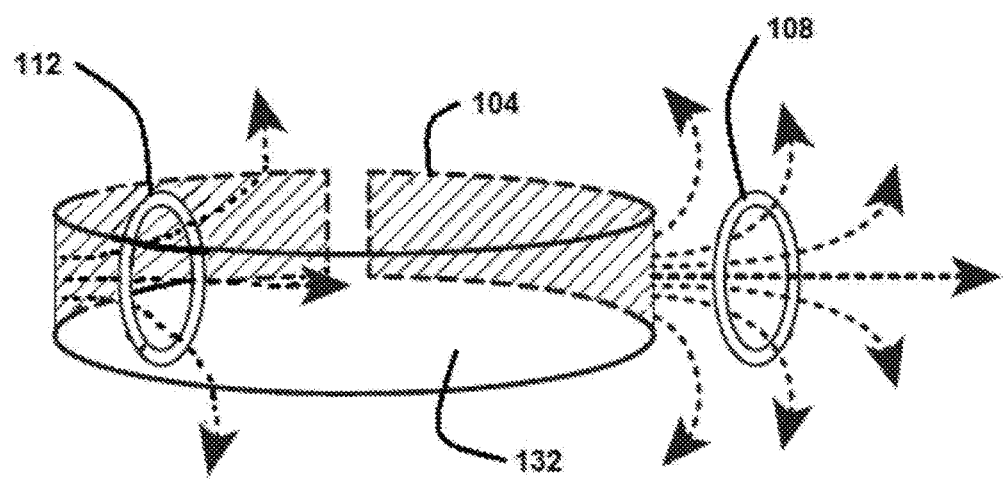

FIGS. 4 and 5A-B are further schematic illustrations of the wireless power transfer system 100 of FIG. 1. FIGS. 4 and 5A-B show how a repeater 104 in accordance with the present disclosure may be oriented in different positions while maintaining coupling and thus power transfer with an adjacent resonator. In one respect, an orientable repeater 104 may be rotated about its central axis while maintaining coupling between the transmitter 108 and the receiver 112 of the wireless power transfer system 100. Thus, as shown in FIG. 4, the orientable repeater 104 may be rotated as indicated by arrow 404. In another respect, the transmitter 108 or receiver 112 may be moved along the length of the orientable repeater 104 while coupling is maintained. As mentioned, a transmitter 108 or receiver 112 positioned adjacent to a given point along the length of the orientable repeater 104 and oriented to be at least not perpendicular with respect to the outwardly facing surface 132 may couple to the orientable repeater 104. Thus, as shown in FIG. 4, the transmitter 108 and the receiver 112 may move along arrows 408 and 412 respectively. Additionally, the transmitter 108 or the receiver 112 may be moved to or otherwise positioned outside of the plane in which the orientable repeater 104 is located. For example, the receiver 112 may be located above the plane in which the orientable repeater 104 is located, as shown in FIG. 5A. The transmitter 108 or the receiver 112 may also be moved to or otherwise positioned inside the orientable repeater 104, as shown in FIG. 5B. In this configuration, coupling exists between the receiver 112 and the orientable repeater 104 because there is additional magnetic flux radiating inward from the inwardly facing surface of the orientable repeater 104.

Figure 6:
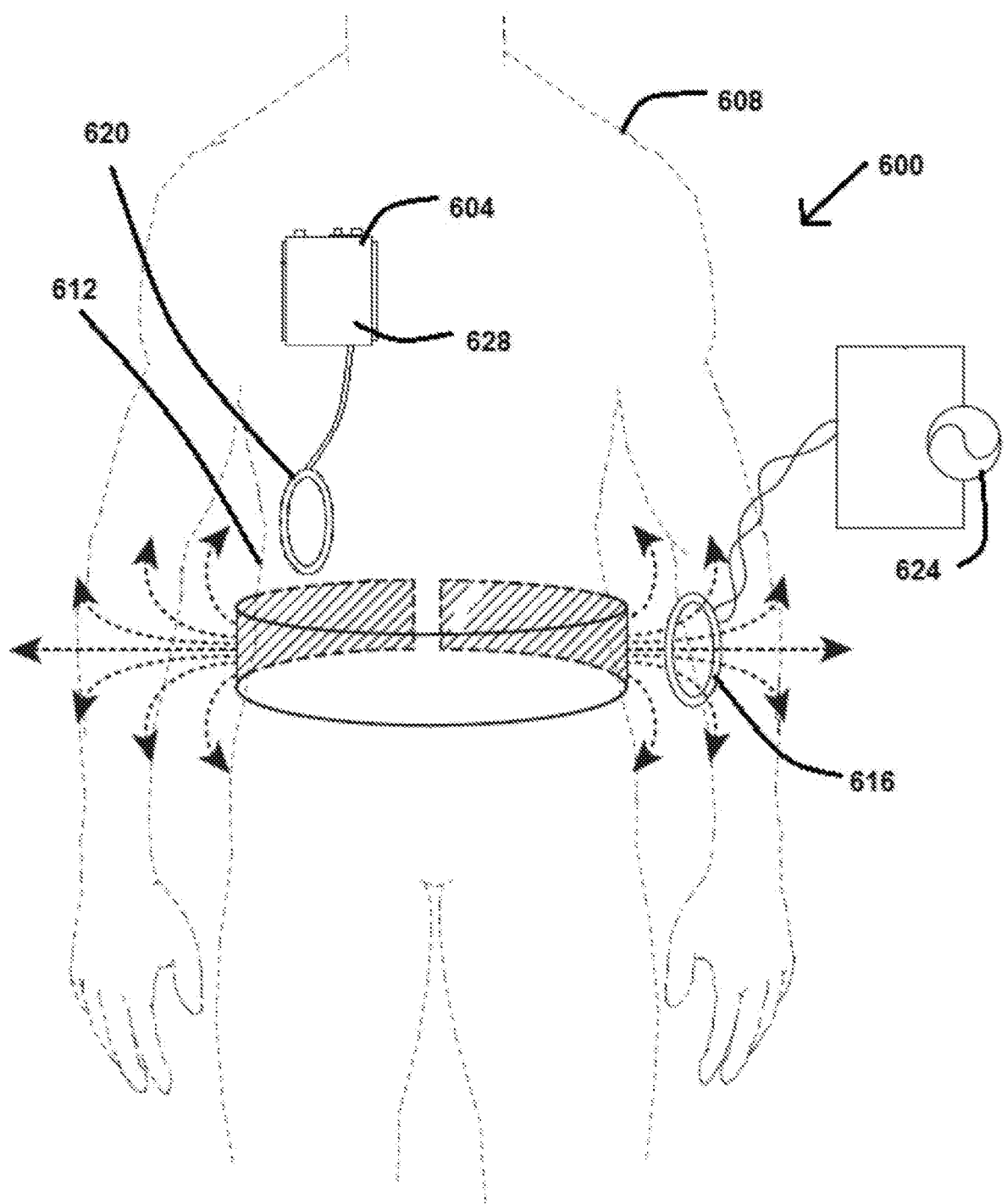
FIG. 6 is a schematic illustration of an implantable system that includes an orientable repeater in accordance with the present disclosure.

In one implementation, an orientable repeater 104 may be used in connection with a transcutaneous energy transfer system. Generally, a transcutaneous energy transfer system operates to transfer electric power to an implanted medical device. The medical device may be implanted in a subject and can include an artificial heart or ventricle assist device. In one respect, the orientable repeater 104 enables power transfer to occur at various points on or near the body of the subject within whom the medical device is implanted. In this way, the subject may gain greater flexibility and higher levels of convenience in connection with use of the transcutaneous energy transfer system. FIG. 6 is a schematic diagram of an implantable system 600 that includes an orientable repeater 104 in accordance with the present disclosure. The implantable system 600 may include an implantable device 604 that is capable of being implanted in a subject, such as a heart pump, an artificial heart, a right ventricular assist device, a left ventricular assist device, a BIVAD, a minimally invasive circulatory support system, a cardiac pacemaker, and so on. While the implanted device 604 may be any implantable medical device, this disclosure describes the implantable system 600 in the context of a heart pump by way of example and not by way of limitation.

The implanted medical device 604 may be configured to receive electrical power from one or more power sources having components which are wholly or partially implanted within the subject and/or which are externally located. In some implementations, the implanted medical device 604 receives electrical power that is wirelessly transmitted through the skin of the subject 608 through the operation of a transcutaneous energy transfer system (TETS) 612. The transcutaneous energy transfer system 612 may include a primary resonant network 616 that is located externally from the subject 608 and a secondary resonant network 620 that is implanted within the subject 608. The primary 616 and secondary 620 resonant networks may include inductive coils so as to together form a coupled resonator system, with the external coil acting as a primary winding and the internal coil acting as a secondary winding. The coils and capacitors associated with the coils may be connected to form a resonant circuit. The coils may be tuned to the same or different resonant frequencies. For example, the coils may be series tuned to a power transmission frequency of about 200 kHz. The external coil may be driven by power source 624 that provides an alternating current which induces a corresponding electric current in the internal coil due to the coupling between the coils. The current induced in the internal coil can then be used to provide electrical power for the implanted medical device 604 or other components of the implanted system 600.

One or more of the implantable medical device 604 and the transcutaneous energy transfer system 612 may connect to each other through a header that forms a portion of a converter 628, controller, and/or other component of the implantable system 600. The converter 628 may be disposed between the implanted medical device 604 and the transcutaneous energy transfer system 612 and is configured to convert power output from transcutaneous energy transfer system 612 into a form that is usable by the implanted medical device 604. Here, the converter 628 may first receive alternating current from the transcutaneous energy transfer system 612 at a frequency that is a function of the resonant frequency of the resonant circuit that is associated with the transcutaneous energy transfer system 612. The converter 628 may then convert the electric energy from this alternating current into a form that is usable by the implanted medical device 604, which in some implementations includes a three-phase motor. In some implementations, converter 628 includes a controller or control system that includes processing units and circuitries for controlling the operation of the implantable device 604 or other portions of the implantable system 600.

In some implementations, the converter 628 or controller component may be configured with an implanted battery, which may be rechargeable. The implantable battery may be configured to provide power to the implantable medical device 604 when power is not available from the transcutaneous energy transfer system 612. For example, during certain time periods, the subject may be located away from the external resonant network portion of the transcutaneous energy transfer system 612 or the external network may be unavailable for other reasons. Here, the implanted system 600 may switch to receive electrical power from the battery so as to maintain an uninterrupted supply of electrical power to the implanted medical device 604. The implanted battery may be rechargeable and, in some embodiments, may be recharged by electrical power transfer received through the operation of the transcutaneous energy transfer system 612.

Figure 7:
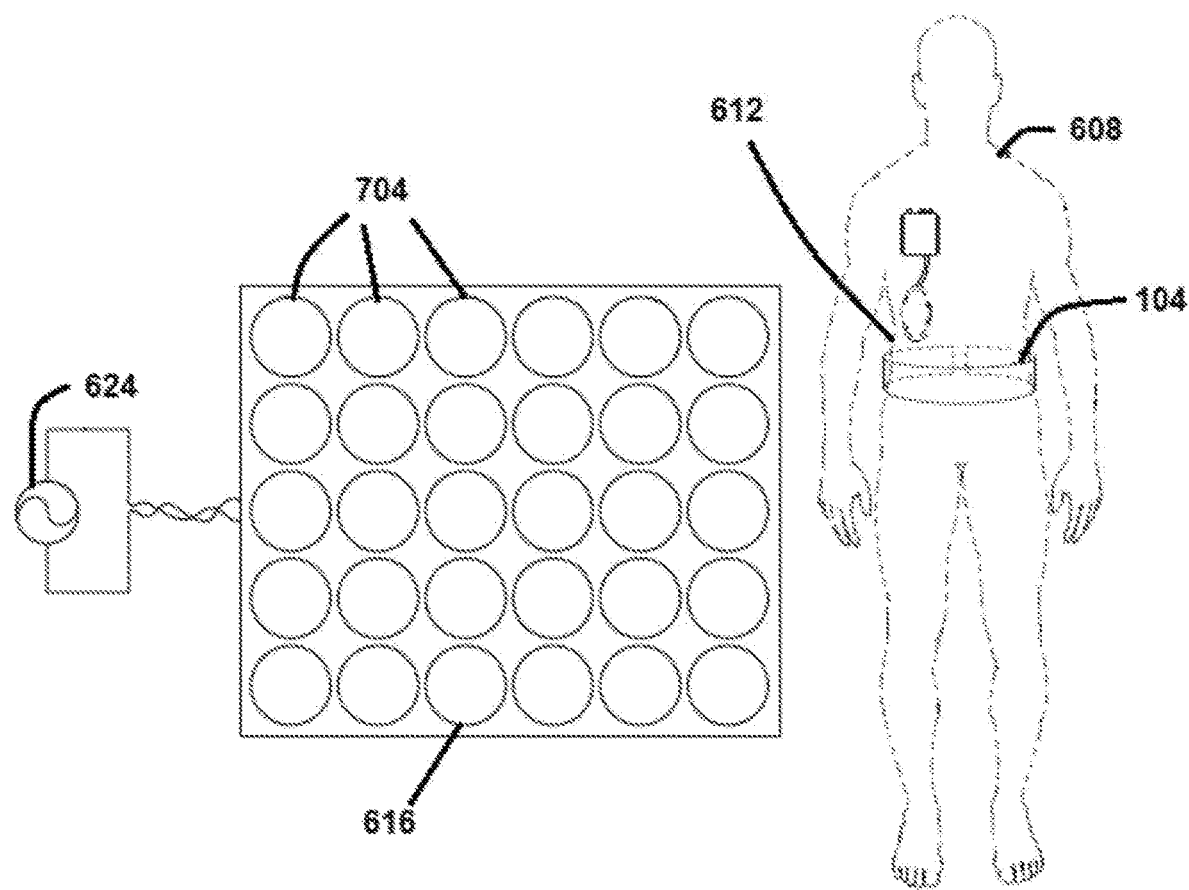
FIG. 7 is a schematic illustration of an implantable system that includes an orientable repeater provided in association with an array of external coils.

As shown in FIG. 6, the transcutaneous energy transfer system 612 may include an orientable repeater 104 in accordance with present disclosure. Because the orientable repeater 104 has a generally circular configuration, the orientable repeater 104 may be sized or otherwise arranged as a belt that is worn around the waist or other area of the subject 608. In this position, the orientable repeater 104 may be interposed between the primary resonant network 616 and the secondary resonant network 620 such that power is transferred from the primary resonant network 616, to the orientable repeater 104, and then to the secondary resonant network 620. In one respect, the orientable repeater 104 allows power transfer to be achieved across distances that are greater that what would be possible with only the primary resonant network 616 and the secondary resonant network 620. In another respect, the orientable repeater 104 provides greater freedom of movement for the subject 608. Because the orientable repeater 104 provides for power transfer at a variety of points and in variety of orientations, the subject 608 may move about to a certain extent and still maintain a continuous power transfer. For example, as shown in FIG. 7, an orientable repeater 104 may provide for a transcutaneous energy transfer system 612 to be used in combination with an array of coils 704 each of which may operate as primary resonant network 616. Here, each coil 704 may be configured to transfer power from a power source 624. To conserve power, the power source 624 may be configured to provide power only to those coils 704 in the array that are in close proximity to the orientable repeater 104 worn by the subject 608.

Figure 8:
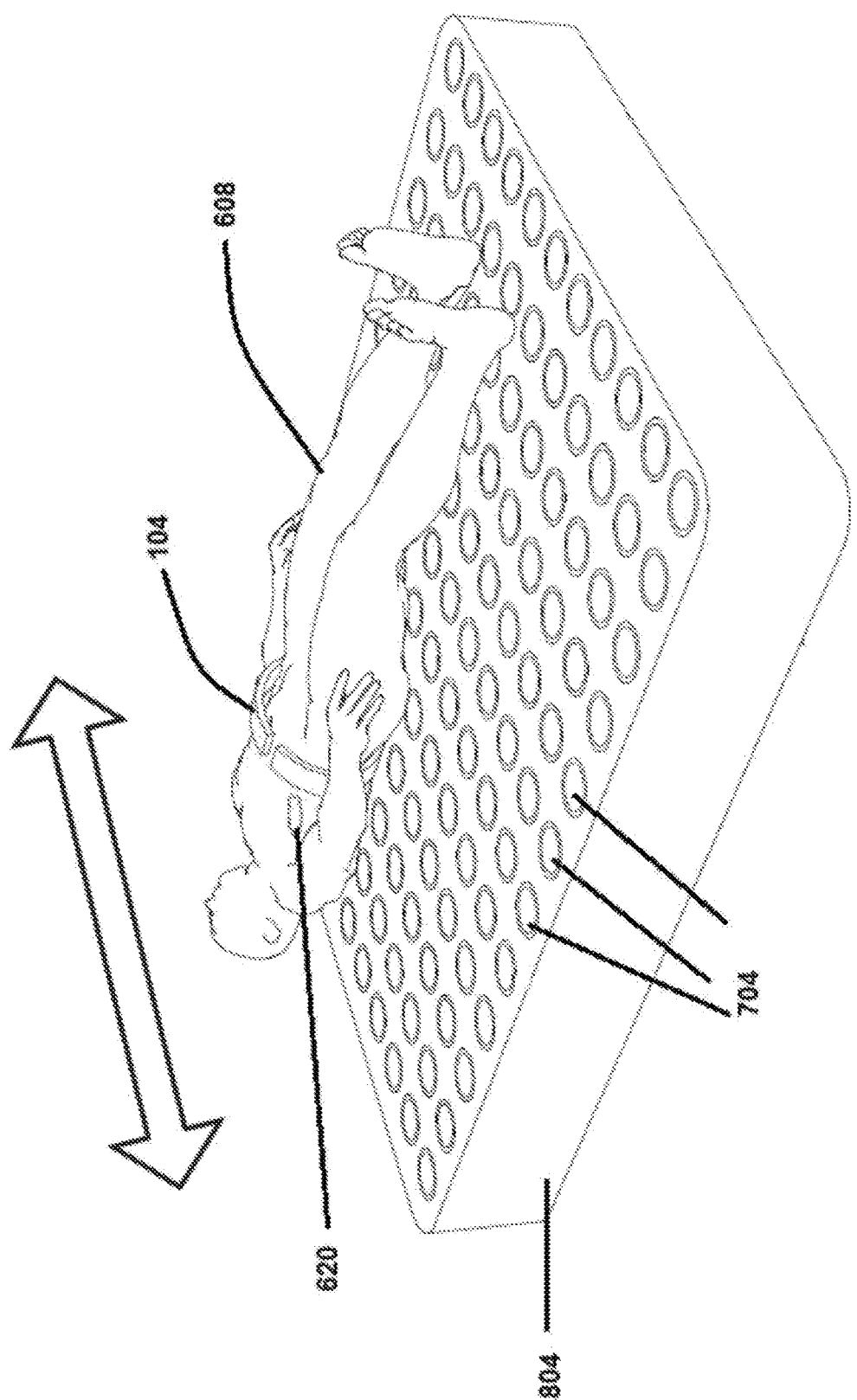
FIG. 8 is a schematic illustration of an implementation that features an array of coils that are incorporated into a mattress.
Figure 9:
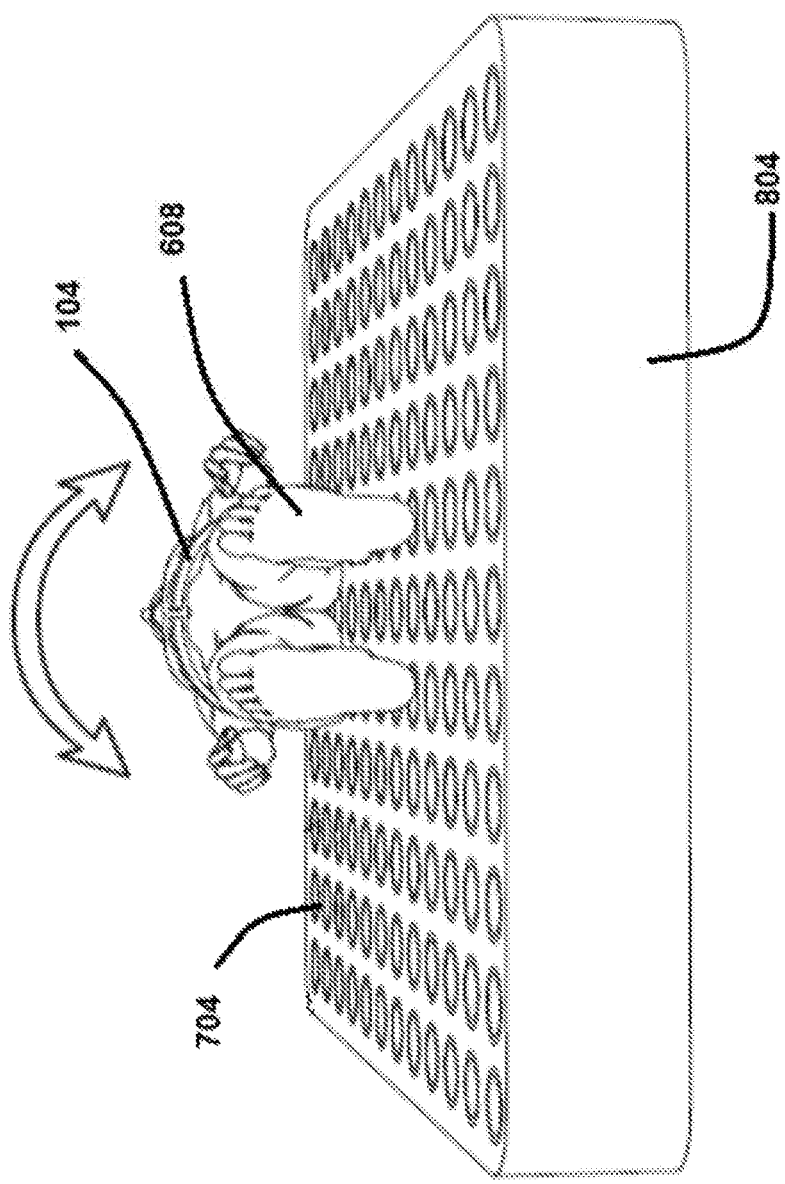
FIG. 9 is a further schematic illustration of an implementation that features an array of coils that are incorporated into a mattress.
Figure 10:
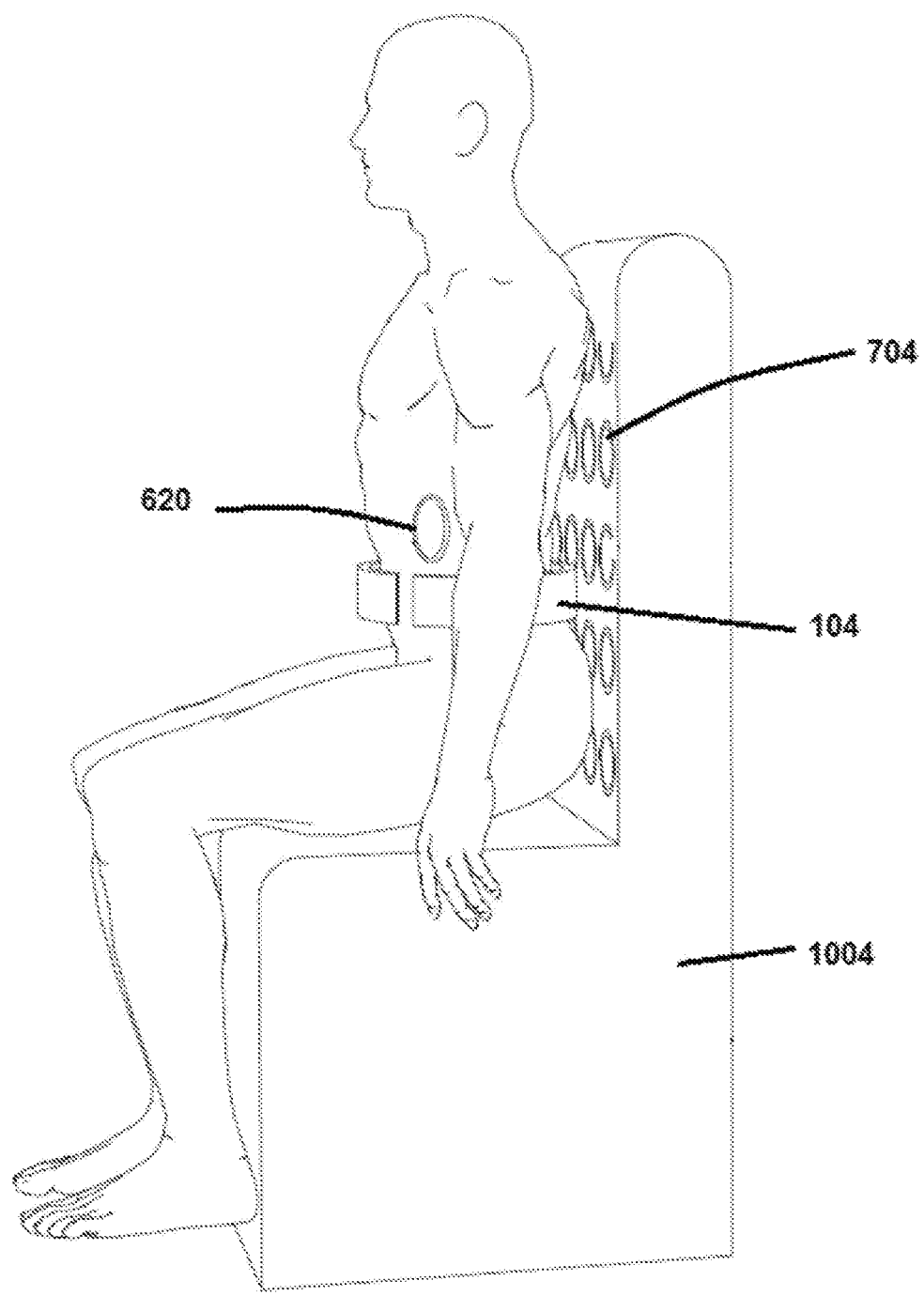
FIG. 10 is a schematic illustration of an implementation that features an array of coils that are incorporated into a chair.
Figure 11:
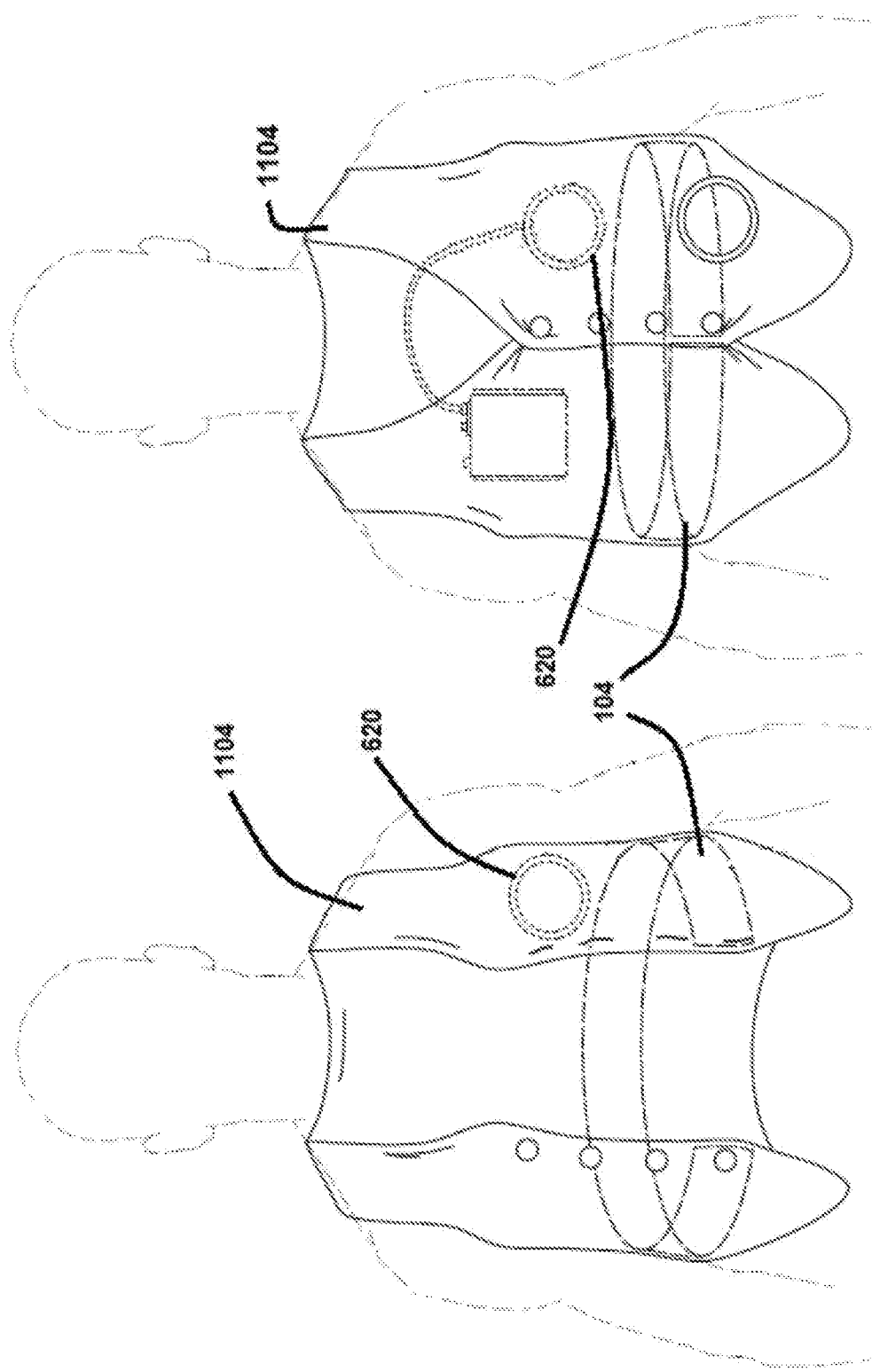
FIGS. 11A-11B is a schematic illustration of an implementation that features an orientable repeater that is sewn into or otherwise incorporated in a shirt or vest to be worn be a subject within whom a medical device is implanted.

FIGS. 8-9 illustrate an implementation that features an array of coils 704 that are incorporated in a mattress 804. Here, the array of coils 704, along with possibly the power source 624, is disposed within the interior of the mattress 804. The subject 608 receives a power transfer from the power source 624 by lying on the mattress 804 while wearing the orientable repeater 104 around his or her waist. Because power transfer is unaffected as long as any particular coil 704 in the array is generally adjacent to any point on the orientable repeater 104, the subject 608 is generally free to move about on the mattress 804 while still receiving a continuous power transfer. For example, the subject 608 may move longitudinally along the surface of the mattress 804, as shown in FIG. 8. By way of further example, the subject 608 may move across the surface of the mattress 804 in a rolling motion as shown in FIG. 9. It should be appreciated that the array of coils 704 is not limited to being placed in a mattress, but may instead be placed in other objects used by the subject 608. For instance, the array of coils 704 may be placed in a chair 1004, such as illustrated in FIG. 10. Additionally, in some implementations, the orientable repeater 104 may be sewn into or otherwise incorporated in a shirt or vest 1104, as shown in FIGS. 11A-11B. Here, the shirt or vest 1104 may function as a convenient mechanism for maintaining the various coils in alignment for efficient power transfer.

An orientable repeater 104 in accordance with the present disclosure may allow for a greater separation between the primary resonant network 616 and the secondary resonant network 620 in a transcutaneous energy transfer system 612. Specifically, orientable repeater 104 can be used to separate the subject or patient from certain components of the primary resonant network 616. This aspect of the present disclosure may be advantageously used during the implantation process. In one respect, the orientable repeater 104 allows the primary resonant network 616 to remain outside the sterile field. Here, the orientable repeater 104 may be used during implantation to provide power as needed to the implant. Once the implantation is complete, the orientable repeater 104 can be removed, sterilized, and used again for the next implantation.

While the present disclosure primarily discusses TETS applications, it should be appreciated that an orientable repeater 104 may be used in various other applications. Indeed, an orientable repeater 104 in accordance with the present disclosure may be used in any application, implementation, or environment that calls for the transfer of electromagnetic energy through the use of coupled resonators. Repeater embodiments are generally configured to maintain coupling in various angular orientations of the repeater and in various positions of adjacent resonators. These features are particularly advantageous in applications that call for relative freedom of movement of the repeater, the transmitter, or the receiver. In medical or surgical applications, an orientable repeater 104 may be used to transfer power to devices that are configured for wireless power transfer. For example, an orientable repeater 104 may be used to transfer power to medical robots, surgical tools, monitoring equipment, sensors, and so on. In household applications, an orientable repeater 104 may be used to transfer power to appliances, television remote controls, cellular phones, lighting, thermostats, and so on.

Figure 12:
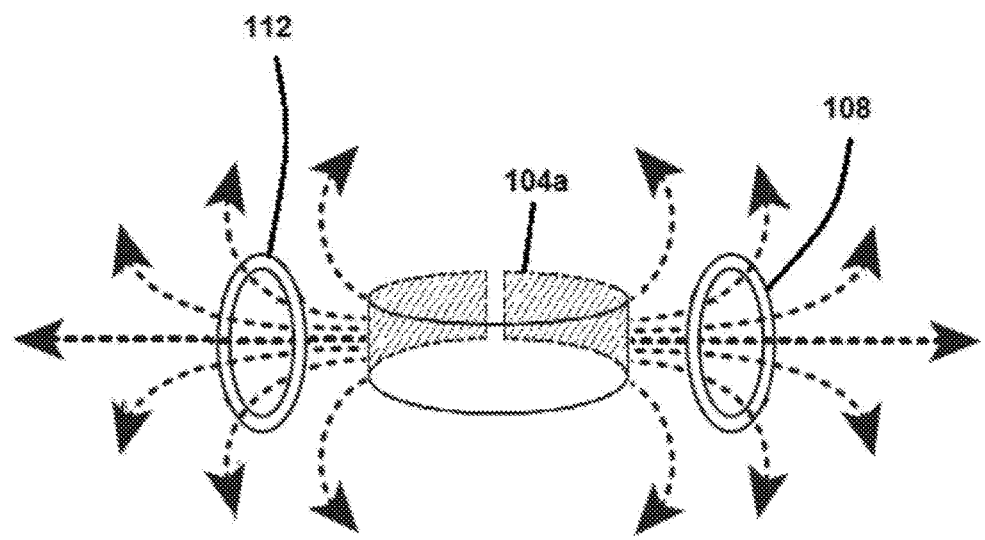
FIG. 12 is a schematic illustration of orientable repeater that is relatively smaller in comparison with the repeater shown in FIG. 1.

An orientable repeater in accordance with the present disclosure may be sized as appropriate for the particular application in which the repeater is to be used. For example, FIG. 12 is a schematic illustration of orientable repeater 104a that is relatively smaller in comparison with the repeater shown in FIG. 1. The repeater 104a of FIG. 12 may be used in applications that call for smaller dimensions such as surgical tools or the like.

Figure 13A:
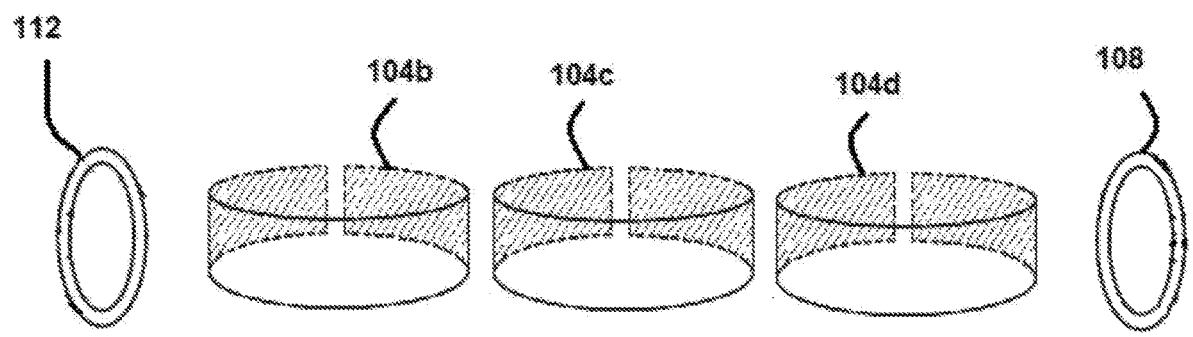
FIG. 13A is a schematic illustration of an example wireless power transfer system that includes a plurality of orientable repeaters.

In some applications, more than one orientable repeater may be interposed between a transmitted and receiver. FIG. 13A is a schematic illustration of a system that includes three repeaters 104b-d by way of example and not limitation. Here, power is transferred from the transmitter 108, down a chain of repeaters 104b-d, and to the receiver 112 arranged at the opposite end of the chains of repeaters 104b-d. In this configuration, the energy transfer may turn corners or otherwise follow a non-liner path due to the angular independence of repeater's coupling. In this and other configuration, an orientable repeater may be embedded in furniture, equipment, fixtures, walls or other structures in a way that facilitates energy transfer between resonators.

Figure 13B:
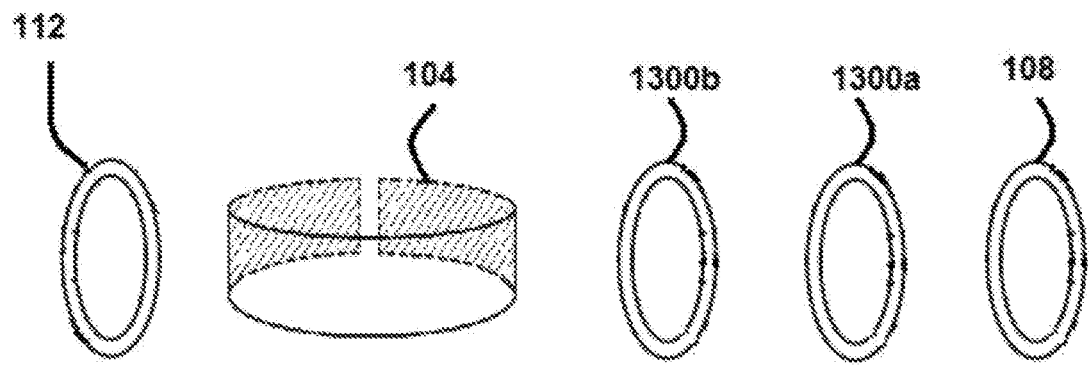
FIGS. 13B-C are schematic illustration of example wireless power transfer system that includes an orientable repeaters used in combination with convention planar repeaters.
Figure 13C:
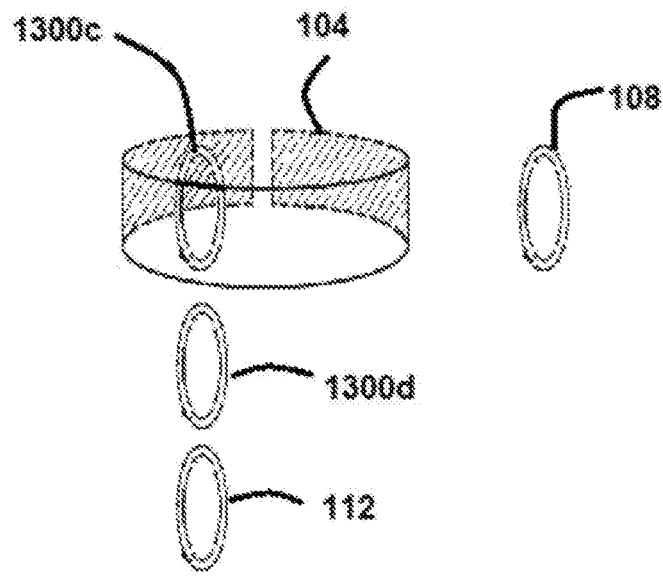

An orientable repeater 104 in accordance with the present disclosure may also work with conventional planar repeaters. FIG. 13B is a schematic illustration of a system that includes an orientable repeater 104 arranged as the third repeater in a series of three repeater, where the first 1300a and second 1300b repeaters are conventional planar repeaters. Here, power is transferred from the transmitter 108, down the chain of repeaters 104, 1300a-b, and to the receiver 112 arranged at the opposite end of the orientable repeater 104. By way of further example, FIG. 13C is schematic illustration of a system that includes an orientable repeater 104 arranged as the first repeater in a series of three repeater, where the second 1300c and third 1300d repeaters are conventional planar repeaters. In FIG. 13C, the second 1300c is disposed inside the orientable repeater 104 in a similar arrangement as that of FIG. 5B. Here, power is transferred from the transmitter 108, down the chain of repeaters 104, 1300c-d, and to the receiver 112 arranged at the opposite end of the third repeater 1300d.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The foregoing description has broad application. The discussion of any embodiment is meant only to be explanatory and is not intended to suggest that the scope of the disclosure, including the claims, is limited to these examples. In other words, while illustrative embodiments of the disclosure have been described in detail herein, the inventive concepts may be otherwise variously embodied and employed, and the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more aspects, embodiments, or configurations for the purpose of streamlining the disclosure. However, various features of the certain aspects, embodiments, or configurations of the disclosure may be combined in alternate aspects, embodiments, or configurations. Moreover, the following claims are hereby incorporated into this Detailed Description by this reference, with each claim standing on its own as a separate embodiment of the present disclosure.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative sizes reflected in the drawings attached hereto may vary.

The invention claimed is:

1. A wireless power transfer system, comprising:
a first resonator;
a repeater resonator configured to inductively couple to the first resonator and to receive electromagnetic energy from the first resonator, wherein the repeater resonator has a length from a first end of the second end, wherein the repeater resonator forms a circular configuration with the first end adjacent to the second end, wherein the repeater resonator includes a series of coils arranged uniformly along the length of the repeater resonator is uniform along the length of the repeater resonator such that the inductive coupling between the repeater resonator and the first resonator is independent of an angular position of the repeater resonator; and
a second resonator configured to inductively couple to the repeater resonator and to receive electromagnetic energy from the repeater resonator, wherein the inductively coupling between the second resonator and the repeater resonator is independent of the angular position of the repeater resonator;
wherein the repeater resonator is configured to be worn as a belt around a subject within whom a medical device and the second resonator are implanted such that the series of coils is distributed around the subject, the repeater further configured to transfer power to the second resonator through a skin of the subject;
wherein the series of coils of the repeater resonator are electrically coupled together in a series configuration.

2. The wireless power transfer system of claim 1, wherein the coupling between the repeater resonator and the first and second resonators is independent of a position of the first and second resonators along a length of the repeater due to the uniform arrangement of the series of coils in the repeater resonator.

3. The wireless power transfer system of claim 1, wherein: the first resonator is configured to electrically connect to a power source and configured as a transmitter; and the second resonator is configured to electrically connect to a circuit load and configured as a receiver.

4. The wireless power transfer system of claim 3, wherein: the circuit load includes the implanted medical device; the second resonator includes an implanted power transfer coil arranged to provide power to the implanted medical device; and the repeater is configured to be worn around a waist of the subject within whom the medical device and the second resonator are implanted.

5. The wireless power transfer system of claim 4, wherein the first resonator includes an array of power transmission coils embedded within a mattress.

6. The wireless power transfer system of claim 4, wherein the first resonator includes an array of power transmission coils embedded with a chair.

7. The wireless power transfer system of claim 1, wherein the repeater resonator is a first repeater resonator and at least one of the first and second resonators is a second repeater resonator.

* * * * *